United States Patent
Brennan et al.

(10) Patent No.: US 12,144,544 B2
(45) Date of Patent: *Nov. 19, 2024

(54) AMETROPIA TREATMENT TRACKING METHODS AND SYSTEM

(71) Applicant: Johnson & Johnson Vision Care, Inc., Jacksonville, FL (US)

(72) Inventors: Noel A. Brennan, Jacksonville, FL (US); Xu Cheng, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 758 days.

This patent is subject to a terminal disclaimer.

(21) Appl. No.: 17/143,008

(22) Filed: Jan. 6, 2021

(65) Prior Publication Data
US 2021/0121057 A1    Apr. 29, 2021

Related U.S. Application Data

(63) Continuation of application No. 15/952,335, filed on Apr. 13, 2018, now Pat. No. 10,912,456, which is a
(Continued)

(51) Int. Cl.
*A61B 3/00*  (2006.01)
*A61B 3/10*  (2006.01)
(Continued)

(52) U.S. Cl.
CPC .......... *A61B 3/0025* (2013.01); *A61B 3/1005* (2013.01); *A61B 3/103* (2013.01);
(Continued)

(58) Field of Classification Search
CPC ........ G16H 50/30; G16H 50/20; G16H 50/50; G16H 30/00; G16H 20/40; A61B 5/1073;
(Continued)

(56) References Cited

U.S. PATENT DOCUMENTS

| 6,045,578 A | 4/2000 | Collins et al. |
| 6,626,538 B1 | 9/2003 | Arrowsmith |

(Continued)

FOREIGN PATENT DOCUMENTS

| CN | 105066901 A | 11/2015 |
| EP | 1154302 A1 | 11/2001 |

(Continued)

OTHER PUBLICATIONS

"Extended European Search Report Received for European Patent Application No. 17153507.3", dated Jul. 28, 2017, 7 Pages.
(Continued)

*Primary Examiner* — Travis S Fissel

(57) ABSTRACT

A system, method and computer program product for estimating future axial elongation of an individual's eye as a way to predict and track refractive error progression of an individual. The method includes: receiving, via a computer interface, data relating to refractive change in a prior pre-determined time period for the individual from a reference timepoint; receiving data representing an age of the individual and data representing a current axial length value of the eye as measured at the reference timepoint; calculating, by said processor, a future axial elongation of the eye as a function of the age of the individual, the current axial length value of the eye as measured at the reference timepoint, and the refractive change in the prior pre-determined time period; generating, an output indication of said computed axial elongation of the eye, and using said output indication to select a myopia control treatment for said individual.

23 Claims, 3 Drawing Sheets

Related U.S. Application Data continuation-in-part of application No. 15/007,660, filed on Jan. 27, 2016, now Pat. No. 10,042,181.

(51) Int. Cl.

| | |
|---|---|
| *A61B 3/103* | (2006.01) |
| *G02C 7/02* | (2006.01) |
| *G02C 7/04* | (2006.01) |
| *G16H 20/40* | (2018.01) |
| *G16H 50/20* | (2018.01) |
| *G16H 50/50* | (2018.01) |
| *G16H 30/00* | (2018.01) |

(52) U.S. Cl.
CPC ............ *G02C 7/027* (2013.01); *G02C 7/028* (2013.01); *G02C 7/047* (2013.01); *G16H 20/40* (2018.01); *G16H 50/20* (2018.01); *G16H 50/50* (2018.01); *G02C 2202/24* (2013.01); *G16H 30/00* (2018.01)

(58) Field of Classification Search
CPC ..... A61B 5/1072; A61B 5/107; A61B 5/0073; A61B 5/0059; A61B 3/12; A61B 3/117; A61B 3/112; A61B 3/107; A61B 3/11; A61B 3/103; A61B 3/1005; A61B 3/0025; G02C 2202/24
USPC ....... 351/246, 212, 211, 209, 210, 208, 206, 351/205; 702/166, 158, 155; 600/558
See application file for complete search history.

(56) References Cited

U.S. PATENT DOCUMENTS

| | | |
|---|---|---|
| 8,303,114 B2 | 11/2012 | Berthezene et al. |
| 9,575,334 B2 | 2/2017 | Bakaraju et al. |
| 9,594,258 B2 | 3/2017 | Fujikado et al. |
| 9,622,655 B2 | 4/2017 | Sarver et al. |
| 9,753,309 B2 | 9/2017 | Loertscher et al. |
| 9,763,568 B2 | 9/2017 | Drobe |
| 2002/0154270 A1 | 10/2002 | Halpern et al. |
| 2004/0013609 A1 | 1/2004 | Trier |
| 2007/0161972 A1 | 7/2007 | Felberg |
| 2008/0062380 A1 | 3/2008 | Phillips |
| 2010/0091242 A1 | 4/2010 | Baglini |
| 2011/0242482 A1 | 10/2011 | Olsen |
| 2012/0172854 A1 | 7/2012 | Raymond |
| 2012/0182520 A1 | 7/2012 | Neitz et al. |
| 2014/0104563 A1 | 4/2014 | Bakaraju |
| 2015/0124212 A1 | 5/2015 | Loertscher et al. |
| 2016/0054588 A1 | 2/2016 | Brennan et al. |
| 2016/0100754 A1 | 4/2016 | Dobashi |
| 2016/0150952 A1 | 6/2016 | Raymond et al. |
| 2016/0338947 A1 | 11/2016 | Leahy |
| 2017/0027435 A1 | 2/2017 | Boutinon et al. |

FOREIGN PATENT DOCUMENTS

| | | |
|---|---|---|
| EP | 1967892 A1 | 9/2008 |
| EP | 3199097 A2 | 8/2017 |
| JP | 2008070894 A | 3/2008 |
| JP | 5667730 B1 | 12/2014 |
| KR | 20160062893 A | 6/2016 |
| RU | 2567273 C1 | 11/2015 |
| WO | 2014074636 A1 | 5/2014 |
| WO | 2015070092 A1 | 5/2015 |
| WO | 2015087435 A1 | 6/2015 |
| WO | 2015087436 A1 | 6/2015 |
| WO | 2017218539 A1 | 12/2017 |

OTHER PUBLICATIONS

"Extended European Search Report Received for European Patent Application No. 18168950.6", dated Sep. 27, 2018, 7 Pages.
"Extended European Search Report Received for European Patent Application No. 22168322.0", dated Jul. 27, 2022, 7 pages.
Jiang et al., "Distribution-free Prediction Intervals in Mixed Linear Models", In Statistica Sinica, vol. 12, pp. 537-553, 2002.
Jordan, et al., "Myopia Progression as a Function of Sex, Age, and Ethnicity", In Investigative Ophthalmology & Visual Science, vol. 62, Issue 10, Aug. 2021, pp. 1-10.
Kazuo, et al., "Measurement of Axial Length of Eyes with Incomplete filing of Silicone oil in the Vitreous Cavity using X ray Computed Tomography", In Ophthalmology, Institute of Clinical Medicine, vol. 86, No. 1, Jan. 31, 2022, pp. 47-50.
Luong, et al., "Racial and Ethnic Differences in Myopia Progression in a Large, Diverse Cohort of Pediatric Patients", Invest Ophthalmol Vis Sci., vol. 61, No. 13, pp. 1-8, Nov. 2020.
Mutti D. O. et al., "Refractive Rrror, Axial Length, and Relative Peripheral Refractive Error before and after the Onset of Myopia". In Invest Ophthalmology Visual Science, June , 2007, vol. 48, Issue 6, pp. 2510-2519.
Nixon, et al., "We Can't Predict Future Axial Elongation in Myopic Children with Confidence", 1 Page.
Pan, et al., "Prevalence of Refractive Errors in a Multiethnic Asian Population: The Singapore Epidemiology of Eye Disease Study", In Investigative ophthalmology & Visual Science, vol. 54, Issue 4, pp. 2590-2598, Apr. 1, 2013.
Saw S.-M. et al., "Epidemiology of Myopia", In Epidemiologic Reviews, vol. 18, No. 2, pp. 175-187, Jan. 1, 1996.
U.S. Appl. No. 62/489,666, filed Apr. 25, 2017, 63 pages.
Wang, Bingjie et al., "Factors Related to Axial Length Elongation and Myopia Progression in Orthokeratology Practice", PLoS One, vol. 12, No. 4, Apr. 18, 2017, 14 pages.
Noel Brennan poster "Previous History of Fast Myopic Progression is a Risk Factor for Future Fast Progression" presented at the 2017 Global Specialty Lens Symposium (GSLS), held Jan. 19-22, 2017.
Noel Brennan poster "Algorithm for Predicting Fast Progressors" presented at the 16th International Myopia Conference Sep. 14 to 17, 2017.
U.S. Appl. No. 62/489,666 filed Apr. 25, 2017, Brennan, Noel.

AMETROPIA TREATMENT TRACKING METHODS AND SYSTEM

CROSS-REFERENCE TO RELATED APPLICATIONS

This patent application claims the benefit of U.S. Provisional Patent Application Ser. No. 62/489,666 filed on Apr. 25, 2017, and is a continuation of U.S. Patent Application Ser. No. 15/952,335 filed on Apr. 13, 2018, which was a continuation-in-part of U.S. patent application Ser. No. 15/007,660 filed Jan. 27, 2016 which granted as U.S. Pat. No. 10,042,181 on Aug. 7, 2018.

BACKGROUND OF THE INVENTION

Field of the Invention

The present invention relates to methods and a system for determining myopia progression in an individual by predicting changes in the axial length of the individual's eye based on that individual's past refractive rate of change, and for recommending a myopia control treatment option for controlling refractive progression based on the predicted axial elongation.

Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus light in front of the retinal plane and hyperopic eyes focus light behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example, greater than five (5) or six (6) diopters, which dramatically affects one's ability to function without optical aids. High myopia is also associated with an increased risk of retinal disease, cataract, glaucoma, and myopic macular degeneration (MMD; also known as myopic retinopathy), and may become a leading cause of permanent blindness worldwide. For example, MMD has been related to refractive error (RE) to a degree rendering no clear distinction between pathological and physiological myopia and such that there is no "safe" level of myopia.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia and myopic astigmatism and hyperopia and hyperopic astigmatism respectively.

Emmetropia describes the state of clear vision where an object at infinity is in relatively sharp focus without the need for optical correction and with the crystalline lens relaxed. In normal or emmetropic adult eyes, light from both distant and close objects passing through the central or paraxial region of the aperture or pupil is focused by the crystalline lens inside the eye close to the retinal plane where the inverted image is sensed. It is observed, however, that most normal eyes exhibit a positive longitudinal spherical aberration, generally in the region of about +0.5 Diopters (D) for a 5 mm aperture, meaning that rays passing through the aperture or pupil at its periphery are focused +0.5 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily through changes to the crystalline lens) causes the spherical aberration to change from positive to negative.

U.S. Pat. No. 6,045,578 discloses that the addition of positive spherical aberration on a contact lens will reduce or control the progression of myopia. The method includes changing the spherical aberration of an ocular system to alter the growth in eye length. In other words, emmetropization may be regulated by spherical aberration. In this process, the cornea of a myopic eye is fitted with a lens having increasing dioptric power away from the lens center. Paraxial light rays entering the central portion of the lens are focused on the retina of the eye, producing a clear image of an object. Marginal light rays entering the peripheral portion of the cornea are focused in a plane between the cornea and the retina, and produce positive spherical aberration of the image on the latter. This positive spherical aberration produces a physiological effect on the eye which tends to inhibit growth of the eye, thus mitigating the tendency for the myopic eye to grow longer.

SUMMARY OF INVENTION

A system, method and computer program product for estimating a future axial elongation (change of length) of an eye of an individual and using an axial elongation value as an index of an individual's myopic progression.

The system is computer implemented and runs computer program products having methods to predict an individual's eye growth, i.e., the axial elongation of an individual's eye, based on that individual's past myopia progression rate, and particularly, as a function of refractive change values detected for that individual over a past predetermined time period, i.e., a past progression rate (e.g., over a past year) and other parameters.

The present invention thus may be used to determine an estimation of a refractive change of an individual over a past predetermined time and use this information to be able to predict a value representing a change in axial length of the eye thereby allowing for estimation of myopia progression over a future period of time.

These results can help clinicians detect excessive eye growth at an early age, thereby facilitating decision-making with respect to interventions for preventing and/or controlling myopia.

In accordance with one aspect of the present invention, a computer-implemented method for treating myopia of an individual is provided. The method comprises: receiving, via an interface at a computer, data relating to refractive change in a prior pre-determined time period for the individual from a reference timepoint; receiving, via the interface, data representing an age of the individual and data representing a current axial length value of the eye as measured at the reference timepoint; calculating, by the processor, a future axial elongation of the eye as a function of the age of the individual, the current axial length value of the eye as measured at the reference timepoint, and the refractive change in the prior pre-determined time period; generating, an output indication of the computed axial elongation of the eye via the interface, and using the output indication to select a myopia control treatment for the individual.

In one aspect, the computer-implemented method causes receipt at a computing device of data relating to past refractive changes for the individual; and calculates, from the past refractive changes data, a progression rate of change of refractive change for the individual. This computed rate of change is further annualized to obtain the refractive change for a past year.

Based on the determined progression rate of change of refractive changes for the individual over the past year, the computer-implemented method calculates a future axial elongation of the eye as a value ΔAL according to:

$$\Delta AL = a \times \text{RECIPY}(D) - b \times \text{age} + c \times \text{axial length} - d$$

wherein a, b and c are respective coefficients; d is a constant value in mm, RECIPY represents the refractive change in Diopters, age represents an individual's age in years, and axial length is in mm.

Based on the computed ΔAL for an individual, the methods implemented may recommend an ametropia control treatment, e.g., prescription of use of a myopia control ophthalmic lens, for example, or a myopia control contact lens, specific to that individual.

In accordance with another aspect of the present invention, there is provided a computer system for treating myopia of an individual. The system comprises: a memory for storing instructions; and a processor coupled to the memory, said processor running said stored instructions to: receive, via an interface at the server, data relating to refractive change in a prior pre-determined time period for the individual from a reference timepoint; receive, via the interface, data representing an age of the individual and data representing a current axial length value of the eye as measured at the reference timepoint; calculate a future axial elongation of the eye as a function of the age of the individual, the current axial length value of the eye as measured at the reference timepoint, and said refractive change in the prior pre-determined time period; generate an output indication of said computed axial elongation of the eye via the interface, and use said output indication to select a myopia control treatment for said individual.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF INVENTION

The present invention relates to methods and a system for tracking an individual's refractive error progression over time by estimating a future axial elongation (change of length) of an eye of an individual and using an axial elongation value as an index of an individual's myopic progression.

In one embodiment, a computer implemented system runs computer program products having methods to predict an individual's eye growth, i.e., axial elongation of an individual's eye, based on that individual's past myopia progression rate as a function of refractive change values detected for that individual over a past predetermined time period, i.e., (e.g., over a past year), and other parameters.

In accordance with another exemplary embodiment, the present invention is directed to a method for estimating future myopic progression based on a predicted axial elongation of an eye of an individual, providing a treatment option to reduce, retard, eliminate and potentially reverse progression of myopia in individuals.

Figure 1:
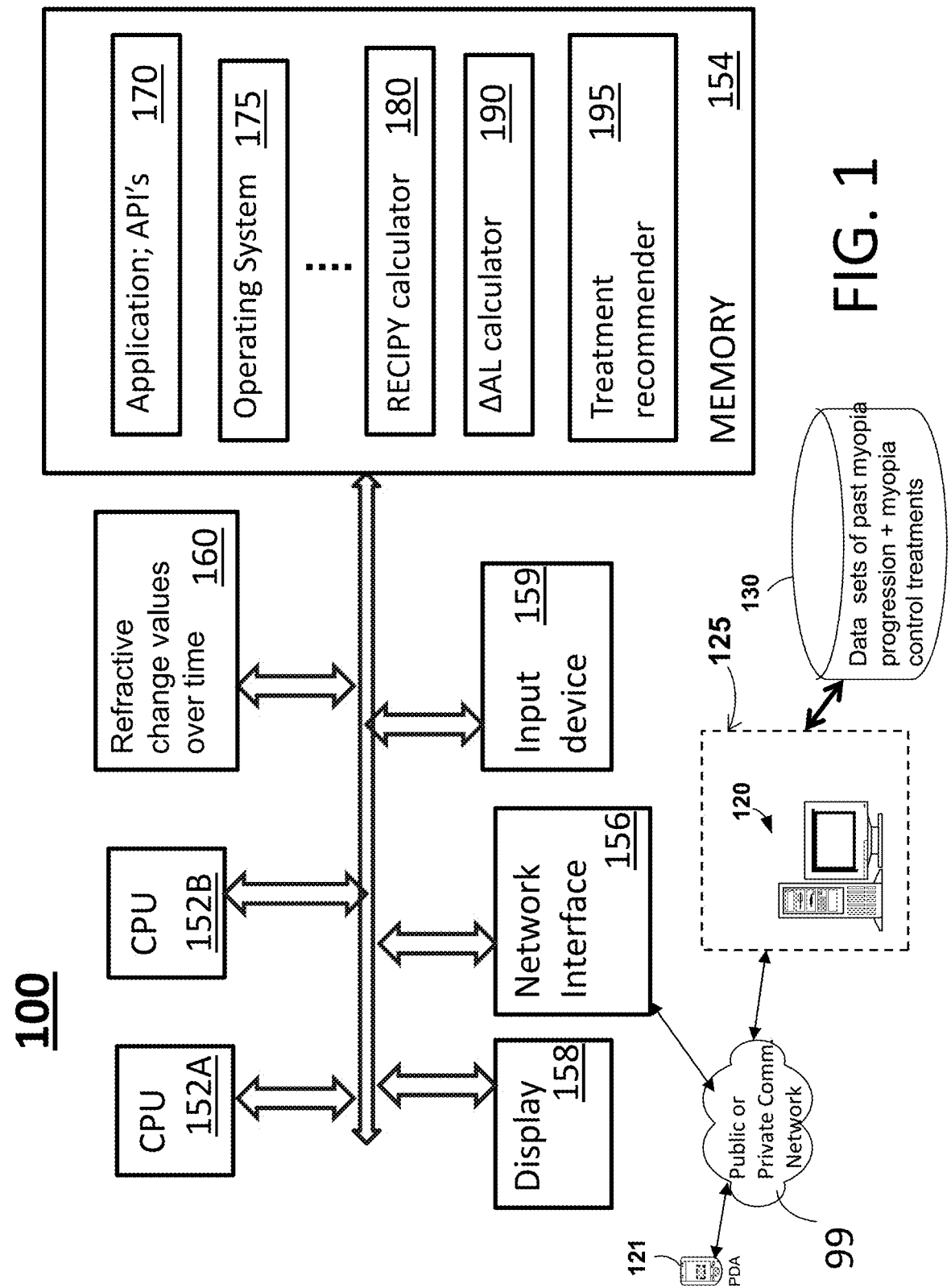
FIG. 1 depicts a computer-implemented system for estimating future axial elongation of an eye of an individual.

FIG. 1 depicts a computer-implemented system for estimating future axial elongation of an eye of an individual and determining a myopia control treatment. In some aspects, system 100 may include a computing device, a mobile device, or a server. In some aspects, computing device 100 may include, for example, personal computers, laptops, tablets, smart devices, smart phones, or any other similar computing device for receiving input data; for performing data analysis such as one or more of the method steps discussed herein, and for outputting data. The input data and output data may be stored or saved in at least one database 130. The input and/or output data may be accessed by a software application 170 installed on computer 100 [for example a computer in the office of an Eye Care Practitioner (ECP)]; by a downloadable software application (app) on a smart device 121; or by a secure website 125 or web link accessible by a computer via network 99. The input and/or output data may be displayed on a graphical user interface of a computer or smart device.

In particular, computing system 100 may include one or more hardware processors 152A, 152B, a memory 154, e.g., for storing an operating system and application program instructions, a network interface 156, a display device 158, an input device 159, and any other features common to a computing device. In some aspects, computing system 100 may, for example, be any computing device that is configured to communicate with a web-site 125 or web- or cloud-based server 120 over a public or private communications network 99. Further, as shown as part of system 100, historical data pertaining to individuals' refractive changes captured from clinicians' measurements and including associated myopia control treatments, are obtained and stored in an attached, or a remote memory storage device, e.g., a database 130.

In the embodiment depicted in FIG. 1, processors 152A, 152B may include, for example, a microcontroller, Field Programmable Gate Array (FPGA), or any other processor that is configured to perform various operations. Processors 152A, 152B may be configured to execute instructions as described below. These instructions may be stored, for example, as programmed modules in memory storage device 154.

Memory 154 may include, for example, non-transitory computer readable media in the form of volatile memory, such as random access memory (RAM) and/or cache memory or others. Memory 154 may include, for example, other removable/non-removable, volatile/non-volatile storage media. By way of non-limiting examples only, memory 154 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 156 is configured to transmit and receive data or information to and from a web-site server 120, e.g., via wired or wireless connections. For example, network interface 156 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 100 to transmit information to or receive information from the server 120.

Display 158 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 158 may include a liquid crystal display (LCD), an e-paper/e-ink display, an organic LED (OLED) display, or other similar display technologies. In some aspects, display 158 may be touch-sensitive and may also function as an input device.

Input device 159 may include, for example, a keyboard, a mouse, a touch-sensitive display, a keypad, a microphone, or other similar input devices or any other input devices that may be used alone or together to provide a user with the capability to interact with the computing device 100.

With respect to the ability of computer system 100 for computing a change in axial length of an individual's eye, the system 100 includes: a memory 160 configured to store data relating to a current individual's past refractive changes/errors, e.g., data received from a clinician over a defined period of time, e.g., a past year. In one embodiment, this data may be stored in a local memory 160, i.e., local to the computer or mobile device system 100, or otherwise, may be retrieved from a remote server 120, over a network. The data relating to a current individual's past refractive changes may be accessed via a remote network connection for input to a local attached memory storage device 160 of system 100.

In one embodiment, the computing system 100 provides a technology platform employing programmed processing modules stored in a device memory 154 that may be run via the processor(s) 152A, 152B to provide the system with abilities for computing future axial elongation length of the eye of an individual based on the input set of historical refractive change data received for that individual.

In one embodiment, program modules stored in memory 154 may include operating system software 170 and a software applications module 175 for running the methods herein that may include associated mechanisms such as APIs (application programming interfaces) for specifying how the various software modules interact, web-services, etc. that are employed to control operations used to carry out the change in axial length computations. One program module 180 stored in device memory 154 may include a "RECIPY" calculator 190 for determining a value ("RECIPY") representative of a current individual's refractive change in a past time period, e.g., one year. From this RECIPY refractive rate of change value of the individual, a further program module 190 stored in device memory 154 may include program code providing the various data and processing instructions of an algorithm that is run by the processors to predict a change in axial length ("$\Delta AL$") value for that individual. Based on the predicted change in axial length ("$\Delta AL$") value for that individual, a further module 195 may be invoked to recommend to a clinician, the individual, or any user, a treatment option(s) such as a type of myopia contact lens, that may be used for inhibiting or preventing refractive changes or reducing a refractive progression rate for the individual.

Figure 2:
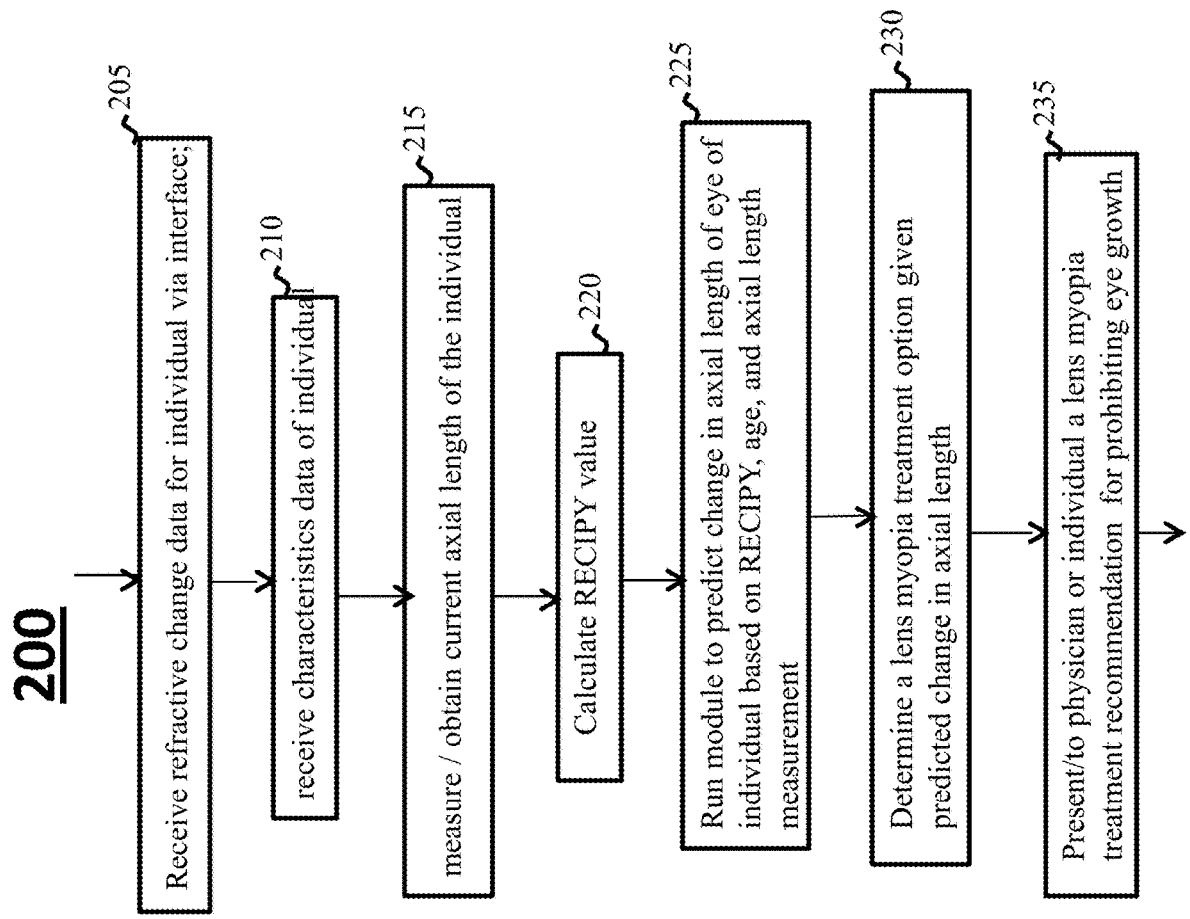
FIG. 2 depicts a method employed for suggesting a treatment option for myopia based on an estimated future axial elongation of an individual's eye according to one embodiment.

FIG. 2 depicts a computer-implemented method 200 run at system 100 for estimating future axial elongation of an individual's eye and for suggesting a treatment option for myopic patients based on an estimated future axial elongation of an individual's eye according to one embodiment. An individual may include children having an approximate age of 6 to 14. However, the methods herein could also be applied to younger children, older adolescents, or young adults.

In one embodiment, the method at 205 receives data representing the refractive values measured for that individual over a period of time. For example, the system 100 of FIG. 1 receives from the memory data representing the refractive change of an individual over a period of time. In one example, a period of time may be one or more years prior to a reference time point, e.g., a current day. Further, at 210 the system of FIG. 1 receives characteristics about the individual including at least, the age of the individual. At 215, the system 100 receives the current measure of the axial length of the eye. If this data is not available, the clinician or ECP may be prompted via a system display interface 158 to obtain or take a current measurement of the axial length of the individual's eye using ultrasonographic, partial coherence interferometry, optical low-coherence reflectometry, swept-source optical coherence tomography or other measurement techniques. From the data representing the refractive values measured for the individual over a period of time, the system invokes the RECIPY calculator module 180 to compute the rate of refractive change value of an individual over a period of time at 220. By annualizing the rate of change, the system calculates the "RECIPY" Refractive Error Change In the Previous Year. For example, if refractive error data is known for 2 years prior to the current date and the change in refraction was −2D, then there would be a RECIPY value of −1D where D is diopters. Although typically measured in clinical practice as refractive error change, future progression is captured as axial elongation as this parameter is a more sensitive measure than refractive error in monitoring progression and is most relevant to the development of myopia related changes, such as myopic retinopathy.

While myopia progression may be characterized by an individual's refractive error change, according to the present embodiment, myopia progression is characterized as the change in axial length of the individual's eye. Continuing to step 225, FIG. 2, the system 100 runs the change in axial length calculator module 190 for predicting a change in axial length of the individual's eye. Equation 1) below represents the predicted change in axial length "ΔAL" as a function of the annualized past rate of refractive change "RECIPY" value, age data received at step 210, and axial length data at the time of making the prediction received at 215.

$$\Delta AL = f(\text{RECIPY}, \text{Age}, \text{Axial Length})$$

specifically, $$\Delta AL = [a(\text{mm/D}) \times \text{RECIPY}(D)] - b(\text{mm/yr}) \times \text{age}(\text{yrs}) + [c \times \text{axial length}(\text{mm})] - d(\text{mm}) \quad (1)$$

where: ΔAL is the estimated axial elongation of the eye, e.g., over the 12-month period after the reference timepoint, and is measured in millimeters, RECIPY is the refractive error change in the prior year (or relativized amount where refraction data is not specifically available for the prior 12-month period) and is measured in diopters D, "age" is the age of the child in years, and "axial length" is the axial length of the eye as measured in mm at the reference timepoint. In one embodiment, coefficient value $a = -0.12051 +/- 0.05162$ (mm/D); coefficient value $b = 0.03954 +/- 0.00323$ (mm/yr); coefficient value $c = 0.036819 +/- 0.001098$; and value $d = 0.35111 +/- 0.025809$ (mm).

It should be understood that, in a further embodiment, equivalent forms of equation 1) for predicting a future axial elongation of the eye as a function of the prior refractive change, current axial length and age of the patient may be implemented. Such a prediction of future refractive change may receive a past axial elongation measurement as an input parameter. Such a prediction of future refractive change may also output a future predicted refractive error change. Further, the form of equation 1) may be modified to receive additional input parameters corresponding to other potential predictors of refractive error progression including, but not limited to: biometric data of the patient or of the patient's eye, such as corneal radius, anterior chamber depth, lens thickness, lens power, vitreous chamber depth or similar, or behavioral aspects of the patient, including but not limited to an amount of time engaged in certain activities, including outdoor activity, levels of close work activity (e.g., number of reading hours per day or week or month or time spent on studying or reading or time spent on digital devices), or information regarding genetic make-up of the patient, including but not limited to: a number of myopic parents or siblings, the refractive status of the patient's parents or siblings, the patient's race, ethnicity, gender, or further parameters including but not limited to a geographic location such as country or degree of urbanization, or any other type of demographic or environmental variables considered relevant to refractive progression.

In one embodiment, equation 1) resulted from a model developed to predict the future ΔAL change in refractive progression according to data from control groups in clinical studies. In an example study, 100 subjects in the control groups have been followed for 2 years and the system obtained cycloplegic autorefraction, and axial length data available at baseline, 12 months and 24 months as well as sex, race and ethnicity data for the subjects. The first 12-month data was used as prior history and the second 12-month data was used as future progression with the 12-month examination set as the date at which the prediction of progression for the second twelve-month period is made (i.e., the 'reference' timepoint). Subjects included in this dataset were children between 8 and 15 years age (mean±SD=9.8±1.3 years) with baseline best-sphere refraction between −0.75D and −5.00D and astigmatism less than or equal to 1.00D. Fifty-one percent of the subjects were female and 93% were Asian. Only the right eyes of the subjects were included in the dataset for analysis. The mean (±SD) of "RECIPY" of this dataset was −0.64±0.52D in refraction change (range: −2.25 to +0.50D). Axial elongation during the first 12-month period was 0.25±0.16 mm (range: −0.18 to 0.65 mm). At the beginning of the $2^{nd}$ year, the mean±SD of spherical equivalent of cycloplegic autorefraction was −3.35±1.26D (range: −1.37 to −6.87D), and the mean±SD of axial length was 24.86±0.87 mm (range: 23.07 to 26.78 mm).

Data available included RECIPY, refractive error and axial length at the reference timepoint, sex, ethnicity and axial elongation in the $2^{nd}$ 12-month period. A multivariate analysis was conducted and yielded equation 1) to relate the variables and obtain:

$$\Delta AL = [-0.12051(\text{mm/D}) \times \text{RECIPY}(D)][-0.03954(\text{mm/yr}) \times \text{age}(\text{yrs})] + [0.036819 \times \text{axial length}(\text{mm})] - 0.35111(\text{mm}).$$

Statistical information on the fits are shown in the Table 1 below where F and P represents statistical values that determine a statistical significance as derived from conducting an analysis of variance. Based on the low P values, it is seen that the RECIPY, Age and Axial Length are significant predictor values.

TABLE 1

| Variable | F | P |
| --- | --- | --- |
| RECIPY | 19.36 | P < 0.0001 |
| Age | 12.13 | P < 0.001 |
| Axial Length | 5.28 | P < 0.05 |

In one embodiment, fast progressors may be considered to have axial elongation above, for example, 0.20 mm. In this case, the equation 1) algorithm exhibits a sensitivity of 0.87 and specificity of 0.58. In one embodiment, the mean progression in those predicted to be fast progressors is 0.301 mm/yr by this criterion and was twice that of those predicted to be slow progressors (0.146 mm/yr). If a cutoff value from the algorithm of 0.23 mm is used to predict those who will progress more than 0.20 mm, the sensitivity is 0.79 with specificity of 0.71.

Table 2 below shows some selected example predictions for axial elongation in the $2^{nd}$ year for the given data at the reference timepoint, i.e., age at reference time point, axial length of the referent time point, and the determined RECIPY value.

TABLE 2

| Age | RECIPY | Axial Length | Predicted Axial Elongation |
| --- | --- | --- | --- |
| Effect of age | | | |
| 7 | −0.500 | 23.5 | 0.298 |
| 8 | −0.500 | 23.5 | 0.258 |
| 9 | −0.500 | 23.5 | 0.219 |
| 12 | −0.500 | 23.5 | 0.100 |
| Effect of RECIPY | | | |

TABLE 2-continued

| Age | RECIPY | Axial Length | Predicted Axial Elongation |
|---|---|---|---|
| 8 | −0.250 | 23.5 | 0.228 |
| 8 | −0.500 | 23.5 | 0.258 |
| 8 | −0.750 | 23.5 | 0.288 |
| Effect of axial length | | | |
| 8 | −0.500 | 23.5 | 0.258 |
| 8 | −0.500 | 24.5 | 0.295 |
| 8 | −0.500 | 25.5 | 0.332 |

Returning to FIG. 2, based on the predicted future ΔAL change in refractive progression, a specific type of soft lens or orthokeratology treatment regime may be recommended. In one embodiment, in FIG. 2 at 230, the system 100 may determine an optical device such as a soft contact lens having a suitable refraction design for use as myopia treatment for the individual given the individual's predicted progression of myopia based on the predicted ΔAL change over the next year. In one embodiment, the treatment option may include a multi-focal contact lens having positive spherical aberration and increasing dioptric power away from the lens center that creates an amount of peripheral "blur" to deprive the eye of light in a manner as known for inhibiting the eye's growth. In other embodiment, it may be determined that a regimen of eye drops or other pharmaceutical treatment administered to the individual may be suitable for reducing the progression of myopia; or a regimen of time spent outdoors may be determined to retard or prevent myopia progression. Any treatment option available now or in the future that may reduce, retard, eliminate or even reverse the progression of myopia in the individual is determined at 230. At 235, FIG. 2, the system may automatically generate a recommendation for the clinician via system display interface 158 whether locally connected to the system or for communication over a network to a remote computer.

In one embodiment, the display may be a graphical user interface of the computer or a smart device (e.g., a tablet computer, smart phone, personal digital assistant, wearable digital device, gaming device, TV). In a specific embodiment, the display may be synchronized on an Eye Care provider's computer or smart device and on a user computer or smart device.

Fast Progressor Prediction

In one embodiment, system 100 may further identify myopes likely to be fast progressors. Detecting of such myopes may be useful for targeting treatment regimens and in designing myopia control clinical studies. As it has been showed that history of fast progression is a factor of similar or better predictive value than age, a well-known risk factor, in assessing likelihood of future fast progression, the algorithm of equation 1) including historical refractive progression (RECIPY) may be used for predicting future fast progression.

In a further example: the system 100 received the Cycloplegic autorefraction (CAR) data and axial length data, (e.g., obtained by partial interferometry) obtained over a time period including at baseline, 1 yr and 2 yrs in 100 children aged 8 to 15 years with −0.75 to −5.00D of myopia. A multivariable regression analysis was conducted with right eye axial elongation during the $2^{nd}$ yr was fit in the multivariable analysis by refractive error change in the previous year (RECIPY), age, gender, ethnicity, 1 yr axial length and 1 yr refractive error. Axial elongation was chosen as the dependent variable because of its better sensitivity in identifying progression, but past refractive change was used as a predictive variable.

Example p-value analysis results for RECIPY, age, 1-year axial length factors are: RECIPY ($p<0.0001$), age ($p<0.001$), 1 yr axial length ($p<0.05$) and RECIPY*age interaction ($p<0.05$) indicating that all these factors contributed significantly in predicting axial elongation between 1 and 2 yrs. Gender, ethnicity and 1 yr refractive error did not contribute significantly to predicting of axial elongation. The model fit accounted for 57% of the variance in axial elongation in the $2^{nd}$ yr. Using a criterion of 0.2 mm, the model has a sensitivity of 0.87 and a specificity of 0.58 in predicting fast progressors. The mean progression in those categorized as fast progressors (0.301 mm/yr) by this criterion was twice that of those predicted to be slow progressors (0.146 mm/yr).

Thus, the computation of ΔAL according to equation 1) provides a good prediction of future axial elongation. This information is useful in guiding myopia control treatment and in design of clinical studies.

Applicant's co-pending U.S. patent application Ser. No. 15/007,660, the whole contents and disclosure of which is incorporated by reference as if fully set forth herein, details a system and method for predicting and tracking an individual's refractive error progression over time. The system and method described are applied to optimally determine a course of treatment for myopia and for an ECP to evaluate over time whether the course of treatment applied for the individual has been/maybe effective. ECPs, parents, and patients are thus provided with a better understanding of the possible long-term benefit of a particular myopia control treatment.

Based on the system, methods, and computer program products, the present invention may assist an ECP to choose a type of myopia control treatment and/or ophthalmic lens for a child based on the computed future axial elongation of the eye and a resulting anticipated progression of myopia.

The methods described in co-pending U.S. patent application Ser. No. 15/007,660 system may be implemented for ECPs to demonstrate and track the effectiveness of treatments to slow the progression of myopia and allow individuals to understand the long-term benefit of a myopia control treatment. The principles described in co-pending U.S. patent application Ser. No. 15/007,660 may be applied to track myopia control treatments to slow the progression of myopia based on the determining of the predicted axial elongation values according to equation 1).

Thus, the tracking methods and system to estimate a potential axial elongation of an individual's eye over a future predetermined period of time relative to a reference population, may be used to: 1) allow ECPs to predict and track axial elongation (and hence, refractive) progression as well as demonstrate and track the effectiveness of treatments to slow the progression of myopia and/or 2) allow patients or parents to understand the long-term benefit of a myopia control treatment.

While the principles discussed herein are directed to myopia, the present invention is not so limited and could be applied to other refractive errors, such as hyperopia or astigmatism.

As will be appreciated by one skilled in the art based on this disclosure, aspects of the present invention may be embodied as a system, method, or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

Computer program code for carrying out operations for aspects of the present invention may be written in any combination of one or more programming languages, including an object-oriented programming language such as Java, Smalltalk, C++, C#, Transact-SQL, XML, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions may be provided to a processor of a general-purpose computer, special purpose computer, or other programmable data processing apparatus to produce a machine, such that the instructions, which execute with the processor of the computer or other programmable data processing apparatus, create means for implementing the functions/acts specified.

These computer program instructions may also be stored in a computer readable medium that can direct a computer, other programmable data processing apparatus, or other devices to function in a particular manner, such that the instructions stored in the computer readable medium produce an article of manufacture including instructions which implement the functions/acts specified.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified.

Figure 3:
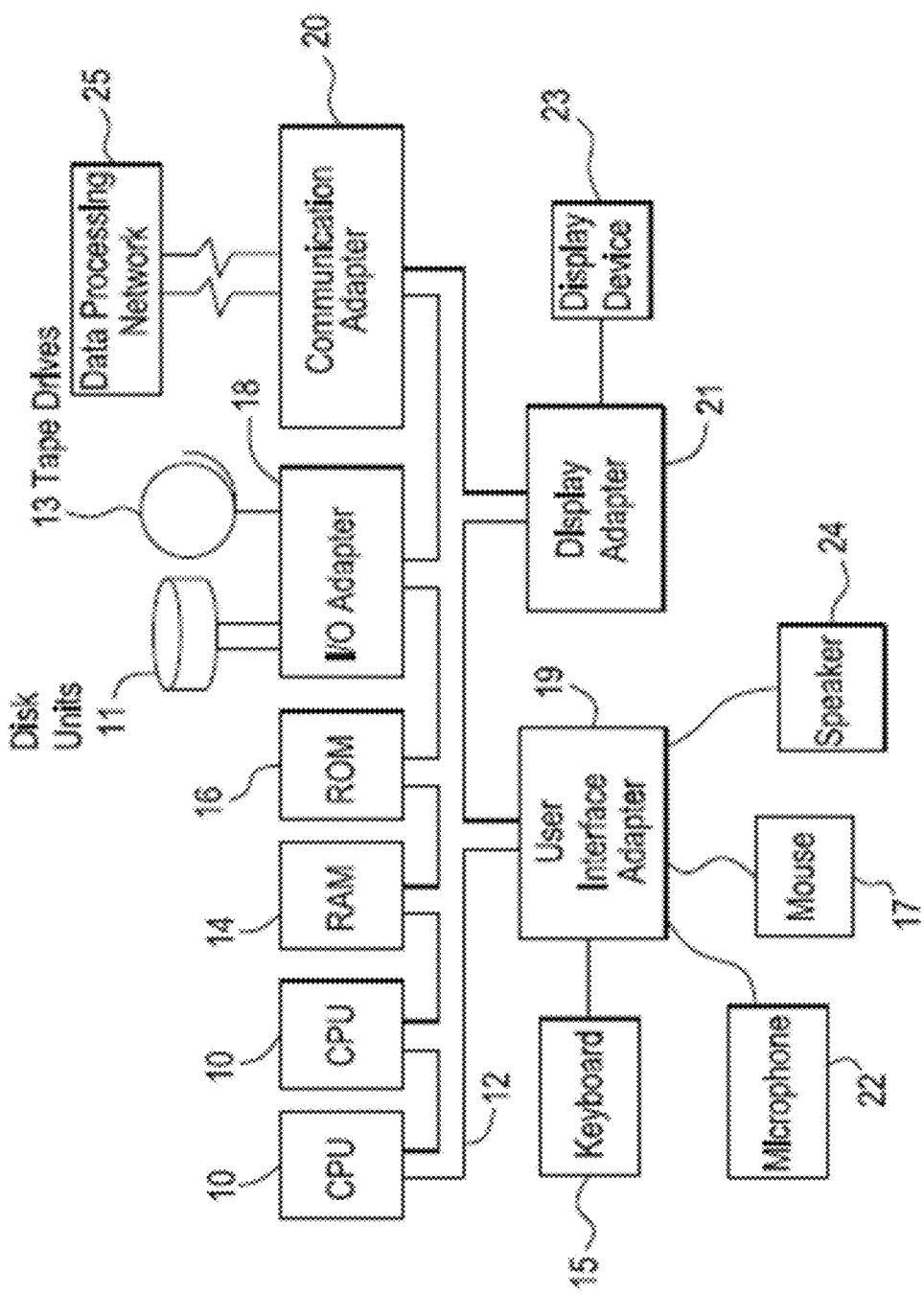
FIG. 3 shows a representative hardware environment for practicing at least one embodiment of the present invention.

Referring now to FIG. 3, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

As used herein, "in communication" includes physical and wireless connections that are indirect through one or more additional components (or over a network) or directly between the two components described as being in communication.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A computer-implemented method for estimating future axial elongation of an individual's eye comprising:
    receiving, via an interface at a computer, data relating to refractive change in a prior pre-determined time period for the individual from a prior date to a current date, the current date being a reference timepoint;
    receiving, via the interface, data representing an age of the individual and data representing a current axial length value of the eye of the individual as measured at the reference timepoint;
    predicting and calculating, by a processor of said computer, a future axial elongation of the eye of the individual represented by a numerical value as a function of the age of the individual, the current axial length value of the eye of the individual as measured at the reference timepoint, and said refractive change in the prior pre-determined time period; and generating, an output indication of said predicted future axial elongation of the eye of the individual via the interface including said numerical value.

2. The computer-implemented method of claim 1, further comprising:
calculating, from said past refractive changes data, a progression rate of change of refractive changes for the individual; and
annualizing the computed rate of change to obtain the refractive change for a past year.

3. The computer implemented method of claim 1, further comprising the step of, generating an output indicating a myopia control treatment for said individual based at least in part of said predicted future axial elongation output indication.

4. The computer implemented method according to claim 3, wherein said myopia control treatment comprises a myopia control ophthalmic lens, an orthokeratology or a pharmaceutical treatment regime.

5. The computer-implemented method of claim 4, wherein the myopia control ophthalmic lens comprises a myopia control contact lens.

6. The computer-implemented method of claim 1, further comprising:
comparing, by said processor, the calculated predicted future axial elongation of the eye of the individual against a predetermined threshold value; and
said processor identifying said individual to be a fast progressor when said calculated axial elongation of the eye is greater than said predetermined threshold value.

7. The computer-implemented method of claim 6, wherein said predetermined threshold value is about 0.301 mm/yr.

8. The computer-implemented method of claim 2, wherein said calculated predicted axial elongation of the eye is a value ΔAL, said method comprising calculating ΔAL according to:

$$\Delta AL = a \times \text{RECIPY}(D) - b \times \text{age} + c \times \text{axial length} - d$$

wherein a, b and c are respective coefficients; d is a constant value in mm, RECIPY represents said refractive change in Diopters (D), age represents an individual's age in years, and axial length is in mm.

9. The computer-implemented method of claim 8, wherein a=−0.12051+/−0.05162 (mm/D); coefficient value b=0.03954+/−0.00323 (mm/yr); coefficient value c=0.036819+/−0.001098; and value d=0.35111 (mm)+/−0.025809.

10. A computer system for estimating future axial elongation of an individual's eye comprising: a memory for storing instructions; and
a processor coupled to the memory, said processor running said stored instructions to:
receive, via an interface at the server, data relating to refractive change in a prior pre-determined time period for the individual from a prior date to a current date, the current date being a reference timepoint;
receive, via the interface, data representing an age of the individual and data representing a current axial length value of the eye as measured at the reference timepoint;
predict and calculate a future axial elongation of the eye represented by a numerical value as a function of the age of the individual, the current axial length value of the eye as measured at the reference timepoint, and said refractive change in the prior pre-determined time period; and generate an output indication of said calculated predicted future axial elongation of the eye via the interface including said numerical value.

11. The computer system of claim 10, wherein the stored instructions further configure the processor to:
calculate, from said past refractive changes data, a progression rate of change of refractive changes for the individual; and
annualize the computed rate of change to obtain the refractive change for a past year.

12. The computer system of claim 10, wherein said processor runs further instructions to generate an output indicating a myopia control treatment for said individual based at least in part of said predicted future axial elongation output indication.

13. The computer system of claim 12, wherein said myopia control treatment comprises one or more of: a myopia control ophthalmic lens, a myopia control contact lens, a soft contact lens, an orthokeratology or a pharmaceutical treatment regime.

14. The computer system of claim 10, wherein said processor runs further instructions to:
compare the calculated predicted axial elongation of the eye against a predetermined threshold value; and
identify an individual to be a fast progressor when said calculated axial elongation of the eye is greater than said predetermined threshold value; and
select a myopia control treatment for said fast progressor.

15. The computer system of claim 11, wherein said calculated predicted axial elongation of the eye is a value ΔAL, said processor running further instructions to: calculate ΔAL according to:

$$\Delta AL = a \times \text{RECIPY}(D) - b \times \text{age} + c \times \text{axial length} - d$$

wherein a, b and c are respective coefficients; d is a constant value in mm, RECIPY represents said refractive change in Diopters, age represents an individual's age in years, and axial length is in mm.

16. The computer system of claim 15, wherein a=−0.12051+/−0.05162 (mm/D); coefficient value b=0.03954+/−0.00323 (mm/yr); coefficient value c=0.036819+/−0.001098; and value d=0.35111 (mm)+/−0.025809.

17. A computer program product for estimating future axial elongation of an individual's eye, the computer program product comprising a non-transitory computer readable storage medium having program instructions embodied therewith, the program instructions executable by a processor to perform a method comprising:
receiving, via an interface at a computer, data relating to refractive change in a prior pre-determined time period for the individual from a prior date to a current date, the current date being a reference timepoint;
receiving, via the interface, data representing an age of the individual and data representing a current axial length value of the eye of the individual as measured at the reference timepoint;
predicting and calculating, by said processor, a future axial elongation of the eye of the individual represented by a numerical value as a function of the age of the individual, the current axial length value of the eye as measured at the reference timepoint, and said refractive change in the prior pre-determined time period; and
generating, an output indication of said predicted future axial elongation of the eye of the individual via the interface including said numerical value.

18. The computer program product of claim 17, wherein said program instructions further configure said processor to perform:
- calculating, from said past refractive changes data, a progression rate of change of refractive changes for the individual; and
- annualizing the computed rate of change to obtain the refractive change for a past year.

19. The computer program product of claim 17, wherein said method further comprises using said generated output to select a myopia control treatment for said individual.

20. The computer program product of claim 19, wherein said myopia control treatment comprises a myopia control ophthalmic lens, an orthokeratology or a pharmaceutical treatment regime.

21. The computer program product of claim 20, wherein the myopia control ophthalmic lens comprises a myopia control contact lens.

22. The computer program product of claim 17, wherein said computed predicted axial elongation of the eye is a value $\Delta AL$, said method comprising calculating $\Delta AL$ according to:

$$\Delta AL = a \times \text{RECIPY}(D) - b \times \text{age} + c \times \text{axial length} - d$$

wherein a, b and c are respective coefficients; d is a constant value in mm, RECIPY represents said refractive change in Diopters, age represents an individual's age in years, and axial length is in mm.

23. The computer program product of claim 22, wherein $a=-0.12051+/-0.05162$ (mm/D); coefficient value $b=0.03954+/-0.00323$ (mm/yr); coefficient value $c=0.036819+/-0.001098$; and value $d=0.35111$ (mm)+/−0.025809.

* * * * *